United States Patent [19]

Noguchi et al.

[11] Patent Number: 5,958,869
[45] Date of Patent: Sep. 28, 1999

[54] SURFACTANT, AND TOILETRY OR DETERGENT COMPOSITION CONTAINING THE SAME

[75] Inventors: Yasunobu Noguchi, Kawasaki; Keigo Sano, Tokyo; Tatsuru Tabohashi; Masao Honma, both of Kawasaki, all of Japan

[73] Assignee: Ajinomoto Co., Inc., Tokyo, Japan

[21] Appl. No.: 09/081,242

[22] Filed: May 19, 1998

Related U.S. Application Data

[62] Division of application No. 08/796,741, Feb. 6, 1997.

[30] Foreign Application Priority Data

Feb. 6, 1996 [JP] Japan ................................ 8-020126

[51] Int. Cl.$^6$ ...................................................... C11D 3/33
[52] U.S. Cl. ............................................ 510/490; 510/515
[58] Field of Search ...................................... 510/490, 515

[56] References Cited

U.S. PATENT DOCUMENTS 5,616,552  4/1997  Yoshihara et al. ...................... 510/490

FOREIGN PATENT DOCUMENTS

| | | |
|---|---|---|
| 282816 A2 | 9/1988 | European Pat. Off. . |
| 367205 B1 | 10/1989 | European Pat. Off. . |
| 367205 A1 | 5/1990 | European Pat. Off. . |
| 434345 A1 | 6/1991 | European Pat. Off. . |
| 738710 B1 | 10/1996 | European Pat. Off. . |
| 788832 A1 | 8/1997 | European Pat. Off. . |
| 830856 A1 | 3/1998 | European Pat. Off. . |
| 92940 | 10/1972 | Germany . |
| 48/22417 | 3/1973 | Japan . |
| 48-072118 | 9/1973 | Japan . |
| 49-018824 | 2/1974 | Japan . |
| 49-030695 | 3/1974 | Japan . |
| WO 94/21595 | 9/1994 | WIPO . |

OTHER PUBLICATIONS

Fettee Seifen Anstrichmittel 68. Jahrgang Nr. 11 1966.
Patent Abstracts of Japan, vol. 17, No. 327 (C–1073), Jun. 22, 1993, JP–05–032529, Feb. 9, 1993.
Patent Abstracts of Japan, 49–001604, Jan. 9, 1974.
Patent Abstracts of Japan, 48–022417, Mar. 22, 1973.

*Primary Examiner*—John R. Hardee
*Attorney, Agent, or Firm*—Oblon, Spivak, McClelland, Maier & Neustadt, P.C.

[57] ABSTRACT

Provided is a novel surfactant which is less irritating to the skin or the mucous membrane than prior art surfactants, which exhibits excellent conditioning effects and fabric softening effects, and which can be widely used in a toiletry or detergent composition. Basic amino-acid derivatives or salts thereof obtained by reacting glycidyl ethers with basic amino acids or salts thereof are incorporated into a toiletry or detergent composition or a conditioning agent.

16 Claims, No Drawings

SURFACTANT, AND TOILETRY OR DETERGENT COMPOSITION CONTAINING THE SAME

This application is a Divisional of application Ser. No. 08/796,741, filed on Feb. 6, 1997, now pending.

BACKGROUND OF THE INVENTION

1. Field of the Invention

The present invention relates to a surfactant. More specifically, the present invention relates to a novel surfactant which is less irritating to the skin or the mucous membrane than prior art surfactants, which exhibits excellent hair conditioning effects and fabric softening effects, and which can be widely used in a toiletry or detergent composition or the like.

2. Related Art

A surfactant that is less irritating to the skin or the mucous membrane than prior art surfactants is preferably used in a composition of toiletries such as a face wash, a shampoo, a rinse, a hair conditioner, a body shampoo or the like and in a detergent composition. Further, hair toiletries such as a rinse, a hair conditioner, a hair treatment and the like are expected to have such conditioning effects that these toiletries make the hair smooth and suppress a dry and hard feeling.

Known examples of surfactants that are less irritating to the skin or the mucous membrane include acylamino-acid derivatives such as N-acylglutamic acid salt, N-acylglycine salt, N-acylarginine ethyl ester salt and the like. But the above-mentioned acylamino-acid derivatives give the hair low levels of conditioning effects, and these derivatives are, therefore, not satisfactory as conditioning agents such as a rinse, a hair conditioner and the like. Besides, with regard to the bubbling property, a further improvement thereof has been in demand.

As another surfactant of an amino-acid derivative type, a surfactant formed by adding a glycidyl ether to a neutral amino acid or an acidic amino acid is known. For example, N-(3-alkyl-2-hydroxypropyl)sarcosine and N,N-bis(3-alkyl-2-hydroxypropyl)glycine formed upon using sarcosine and glycine are described in E. Ulsperger, Fette, seifen, anstrichm., 68 (11), 964–967 (1966). Further, N-(3-alkyl-2-hydroxypropyl)serine, N-(3-alkyl-2-hydroxypropyl)aspartic acid and the like are described in WO 94/21595. However, these neutral and acidic amino-acid derivatives give the hair still unsatisfactory conditioning effects.

Furthermore, amino-acid derivatives formed by adding an 1,2-epoxyalkane to an amino acid are described in Japanese Laid-Open Patent Application (Kokai) No. 22,417/1973. However, these amino-acid derivatives are not said to be satisfactory in terms of solubility.

Meanwhile, an alkyl quaternary ammonium salt and the like have been widely used as conditioning agents or fabric softening agents. It has been known that these conditioning agents are electrically adsorbed on the hair surface, which is weakly acidic, or the fabric surface, which is negatively charged in the rinsing water, to impart a good combing property, a smoothness and the like to the hair. Nevertheless, they strongly irritate the skin, the mucous membrane and the like, and are problematic also in terms of biodegradability. Furthermore, they lower the hygroscopic property of fabric.

SUMMARY OF THE INVENTION

It is an object of the present invention to provide a surfactant which is less irritating to the skin, the mucous membrane and the like than prior art surfactants, and which exhibits a high solubility and a high bubble stability as well as to provide a hair toiletry which exhibits excellent conditioning effects of imparting a smoothness to the hair and suppressing a dry and hard feeling of the hair, and a fabric softener which exhibits excellent softening effects and maintains the hygroscopic property of fabric.

Under these circumstances, the present inventors have assiduously conducted investigations, and have consequently found that basic amino-acid derivatives formed by reacting glycidyl ethers which are epoxy compounds with basic amino acids such as arginine, lysine and the like exhibit excellent conditioning effects, excellent softening effects, a low level of irritation, an excellent solubility and an excellent bubble stability. These findings have led to the completion of the present invention. The amino-acid derivatives of the present invention can widely be used in toiletry and detergent compositions, and are especially appropriate as hair toiletries such as a shampoo, a rinse, a treatment and the like.

The surfactant of the present invention contains at least one type of basic amino-acid derivatives or salts thereof, wherein the derivatives are represented by formulas (1) to (4)

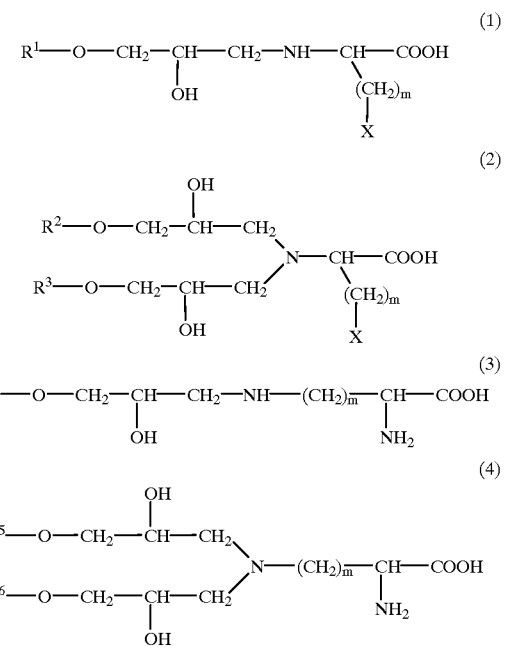

wherein $R^1$ to $R^6$ each represent a linear or branched alkyl or alkenyl group having from 8 to 22 carbon atoms, provided that $R^2$ and $R^3$, or $R^5$ and $R^6$ are the same or different, m represents an integer of from 1 to 5, and X represents any of the following substituents,

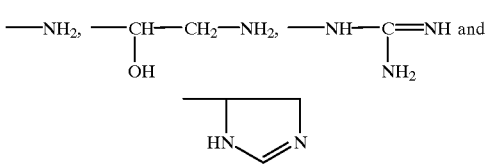

DETAILED DESCRIPTION OF THE PREFERRED EMBODIMENTS

Salts of the basic amino-acid derivatives include inorganic salts such as hydrochloride and a sulfate, and organic acid salts such as an acetate, a citrate, a p-toluenesulfonate, a fatty acid salt, an acidic amino-acid salt and an L- or DL-pyrrolidonecarboxylate.

These basic amino-acid derivatives or salts thereof may be used either singly or in combination.

The basic amino-acid derivatives of formulas (1) to (4) can be easily produced by conventional methods known to those of ordinary skill in the art such as by the same process of treating an amino acid with an epoxyalkane as described in Japanese Laid-Open Patent Application (Kokai) No. 22,417/1973, namely by reacting a basic amino acid with a glycidyl ether represented by formula (8)

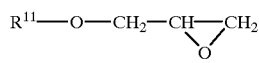
(8)

wherein $R^{11}$ represents a linear or branched alkyl or alkenyl group having from 8 to 22 carbon atoms under alkaline conditions in a lower alcohol or a mixed solvent of a lower alcohol and water.

The above-mentioned glycidyl ether can be obtained by reacting, for example, a natural or synthetic saturated or unsaturated higher alcohol with epichlorohydrin. Examples thereof include decyglycidyl ether, dodecylglycidyl ether, tetradecylglycidyl ether and stearylglycidyl ether. These may be used either singly or in combination. Commercially available examples of the glycidyl ether include Epiol L-41 (decyglycidyl ether) and Epiol SK (stearylglycidyl ether) made by NOF Corporation, Heloxy 8 (mixture of dodecylglycidyl ether and tetradecylglycidyl ether) made by ACI Japan, Ltd., Denacol EX-192 (mixture of dodecylglycidyl ether and tetradecylglycidyl ether) made by Nagase Chemicals, Ltd., and SY-25L (mixture of decylglycidyl and dodecylglycidyl ether) made by Sakamoto Yakuhin Kogyo Co., Ltd.

Examples of the basic amino acid include arginine, lysine, ornithine, histidine and hydroxylysine.

In the case of, for example, lysine and ornithine among the basic amino acids, the moiety that binds to the glycidyl ether is considered to be preferentially an ε-amino group (lysine) and an δ-amino group (ornithine). An α-amino group is also available. A compound obtained by reacting two molecules of the glycidyl ether with an ε-amino group, a δ-amino group or an α-amino group is also included therein. Further, a compound obtained by reacting one molecule of the glycidyl ether with each of an ε-amino group (δ-amino group in ornithine) and α-amino group, and a compound obtained by adding three or four molecules of the glycidyl ether to one molecule of an amino acid may be used.

Amino-acid derivatives obtained by reacting a neutral or acidic amino acid with a glycidyl ether are useful as a surfactant also. Examples of the neutral amino acids include glycine, alanine, β-alanine, sarcosine, N-methyl-β-alanine, valine, leucine, isoleucine, serine, threonine, methionine, phenylalanine, tyrosine, proline, hydroxyproline, homoserine, α-aminobutyric acid, α-aminovaleric acid, α-aminocaproic acid, phenylglycine, cystine, cysteine, 3,4-dihydroxyphenylalanine and γ-aminobutyric acid. Examples of the acidic amino acid include glutamic acid and aspartic acid. However, these neutral or acidic amino-acid derivatives cannot provide satisfactory conditioning effects and softening effects. Incidentally, these neutral or acidic amino acid derivatives may be contained unless the effect of the present invention is impaired.

In the reaction between the glycidyl ether and the amino acid, it is advisable to use the amino acid in the form of an alkali metal salt or to conduct the reaction under alkaline conditions in order to increase reactivity and prevent side reactions. However, with respect to arginine, the reaction could be conducted without using these conditions.

As the reaction solvent, a lower alcohol such as methyl alcohol, ethyl alcohol, n-propyl alcohol or i-propyl alcohol, or a mixed solvent of this lower alcohol and water is ordinarily used. The mixing ratio of the lower alcohol to water varies depending on the types of the amino acid and the glycidyl ether. It may be between 100:0 and 10:90, preferably 1:1 to 2:1. When the amount of the alcohol is small, the solubility of the glycidyl ether is decreased, and the reaction rate is notably reduced.

The reaction temperature varies depending on the type and the composition of the reaction solvent. It is generally between 70° C. and 100° C., preferably between 80° C. and 95° C. It is advisable that the reaction be conducted under reflux. The glycidyl ether may be added at a time before heating, or in divided portions or dropwise continuously after heating is started. In order to control formation of by-products, it is preferable to add the same dropwise continuously after heating is started.

The thus-obtained reaction product sometimes contains, besides the desired amino-acid derivatives, by-products such as an unreacted amino acid, a glycidyl ether hydrolyzate and the like. In this case, purification can be conducted by a known method such as extraction, recrystallization, chromatography or the like. The resulting product may be used in the form of a mixture unless it influences a surface activity.

When a higher alcohol is incorporated into the surfactant of the present invention, the hair conditioning effects can be further increased. That is, the present invention provides a toiletry or detergent composition comprising a surfactant of any of formulas (1) to (4) and a higher alcohol.

This higher alcohol is represented by the formula (9)

$$R^{12}-OH \qquad (9)$$

wherein $R^{12}$ represents a linear or branched alkyl or alkenyl group having from 12 to 36 carbon atoms. Examples thereof which are widely used include cetyl alcohol, stearyl alcohol, behenyl alcohol, isostearyl alcohol, octyl dodecanol and olyl alcohol.

The higher alcohol and the surfactant in the above-mentioned detergent composition can be used at a relatively wide ratio. The weight ratio of the higher alcohol to the surfactant is preferably between 10:100 and 100:0.5, more preferably between 50:100 to 100:5. When it is less than 10:100, the effect provided by the higher alcohol is not sufficiently exhibited. When it is more than 100:5, the conditioning effects are reduced.

The surfactant of the present invention can be incorporated into compositions of toiletries and detergents, for example, hair care products such as a shampoo, a rinse and a treatment, toiletries such as a cleansing cream and a massage cream, a body cleaning agent such as a body shampoo, a sterile detergent, a fabric softener, a kitchen detergent and a cleaning detergent.

The amount of the surfactant in the composition of the present invention can be appropriately determined depending on the use and the formulation. It is generally between 0.1% by weight and 95% by weight. Another surfactant may be jointly used in such a composition unless it impairs the effect of the present invention. Examples of the other surfactant include anioinic surfactants such as a higher fatty acid salt, a polyoxyalkyl ether sulfuric acid salt, an N-acylaminocarboxylic acid salt, a polyoxyethylene alkyl ether carboxylic acid salt, an N-acyltaurine salt and a sulfosuccinic acid surfactant, amphylytic surfactants such as an alkyldimethylaminoacetic acid betaine, a higher fatty acid amide propyldimethylaminoacetic acid betaine and an imidazoline surfactant; nonionic surfactants such as alkyl saccharide surfactants, polyoxyethylene alkyl ether surfactants, higher fatty acid alkanolamide and amine oxide; and cationic surfactants such as an alkyltrimethylammonium chloride and an N-acylarginine lower alkyl ester pyrrolidonecarboxylic acid salt.

In addition to the above-mentioned surfactants, a variety of additives which are ordinarily used can be added. Examples thereof include wetting agents such as ethylene glycol, propylene glycol, 1,3-butylene glycol, glycerol and sorbitol; emulsifying agents such as glycerol monostearate and polyoxyethylene sorbitan monolaurate; hydrocarbons such as liquid paraffin, vaseline and squalane; esters such as isopropyl myristate and octyldodecyl myristate; cellulose derivatives such as hydroxyethyl cellulose, hydroxypropyl cellulose and carboxymethyl cellulose; anioinic polymers such as an acrylic acid polymer; silicon derivatives; and cationic polymers such as cationic guar gum. Further, antibiotics such as paraben derivatives, perfumes, pigments, viscosity modifiers, pearling agents, antioxidants, disinfectants, anti-inflammatory agents, UV absorbers, pH adjustors and crude drugs can be used as required.

EXAMPLES

The present invention is illustrated specifically by referring to the following examples. However, the present invention is not limited to these examples.

Example 1

N-(2-hydroxy-3-dodecyloxypropyl)-L-arginine hydrochloride

L-arginine (17.4 g, 0.1 mols) was dissolved in 100 ml of water in a three-necked round flask, and 100 ml of i-propanol were added thereto. Then, 24.2 g (0.1 mols) of dodecylglycidyl ether (made by Sakamoto Yakuhin Kogyo Co., Ltd.) were added dropwise thereto over a period of 30 minutes while being heat-refluxed and stirred. Further, the mixture was stirred under reflux for 3 hours. It was identified through TLC and gas chromatography that dodecylglycidyl ether disappeared. Thereafter, the resulting mixture was neutralized with 10.1 g (0.1 mols) of 36% hydrochloric acid. The reaction solution was concentrated under reduced pressure, and the residue was purified through silica-gel column chromatography (Kieselgel 60 made by Merck & Co., Inc., eluent=mixture of chloroform, methanol and acetic acid at a ratio of 3:1:0.5) to give 15.0 g of N-(2-hydroxy-3-dodecyloxypropyl)-L-arginine hydrochloride (yield 36.0%).

TLC (mixture of butanol, acetic acid and water at a ratio of 4:1:2): Rf=0.64 ESI mass spectrum: 417.5 (MH+) IR (NaCl, cm$^{-1}$): 3177, 2955, 2920, 2853, 1692, 1628, 1468, 1397, 1377, 1215, 1116

Example 2

N,N-bis(2-hydroxy-3-dodecyloxypropyl)-L-arginine hydrochloride

L-arganine (17.4 g, 0.1 mols) was dissolved in 100 ml of water in a three-necked round flask, and 100 ml of i-propanol were added thereto. Then, 48.4 g (0.2 mols) of dodecylglycidyl ether were added dropwise thereto over a period of 30 minutes while being heat-refluxed and stirred. Further, the mixture was stirred under reflux for 3 hours. It was identified through TLC and gas chromatography that dodecylglycidyl ether disappeared. Thereafter, the resulting mixture was neutralized with 10.1 g (0.1 mols) of 36% hydrochloric acid. The reaction solution was concentrated under reduced pressure, and the residue was purified through silica-gel column chromatography (Kieselgel 60, eluent= mixture of chloroform, methanol and acetic acid at a ratio of 3:1:0.5) to give 11.4 g of N,N-bis(2-hydroxy-3-dodecyloxypropyl)-L-arginine hydrochloride (yield 17.2%).

TLC (mixture of butanol, acetic acid and water at a ratio of 4:1:2): Rf=0.72 ESI mass spectrum: 659.77 (MH+) IR (NaCl, cm$^{-1}$): 3177, 2955, 2920, 2853, 1692, 1628, 1468, 1397, 1377, 1215, 1120

Example 3

N-(2-hydroxy-3-octadecyloxypropyl)-L-arginine hydrochloride

L-arginine (17.4 g, 0.1 mols) was dissolved in 100 ml of water in a three-necked round flask, and 100 ml of i-propanol were added thereto. Then, 32.6 g (0.1 mols) of octadecylglycidyl ether (made by Sakamoto Yakuhin Kogyo Co., Ltd.) were added dropwise thereto over a period of 30 minutes while being heat-refluxed and stirred. Further, the mixture was stirred under reflux for 3 hours. It was identified through TLC and gas chromatography that octadecylglycidyl ether disappeared. Thereafter, the resulting mixture was neutralized with 10.1 g (0.1 mols) of 36% hydrochloric acid. The reaction solution was concentrated under reduced pressure, and the residue was purified through silica-gel column chromatography (Kieselgel 60, eluent=mixture of chloroform, methanol and acetic acid at a ratio of 3:1:0.5) to give 21.2 g of N-(2-hydroxy-3-octadecyloxypropyl)-L-arginine hydrochloride (yield 42.3%).

TLC (mixture of butanol, acetic acid and water at a ratio of 4:1:2): Rf=0.64 ESI mass spectrum: 501.5 (MH+) IR (NaCl, cm$^{-1}$): 3175, 2955, 2917, 2851, 1692, 1628, 1468, 1377, 1215, 1121

Example 4

N,N-bis(2-hydroxy-3-octadecyloxypropyl)-L-arginine hydrochloride

L-arginine (17.4 g, 0.1 mols) was dissolved in 100 ml of water in a three-necked round flask, and 100 ml of i-propanol were added thereto. Then, 65.2 g (0.2 mols) of octadecylglycidyl ether were added dropwise thereto over a period of 30 minutes while being heat-refluxed and stirred. Further, the mixture was stirred under reflux for 3 hours. It was identified through TLC and gas chromatography that octadecylglycidyl ether disappeared. Thereafter, the resulting mixture was neutralized with 10.1 g (0.1 mols) of 36% hydrochloric acid. The reaction solution was concentrated under reduced pressure, and the residue was purified through silica-gel column chromatography (Kieselgel 60, eluent= mixture of chloroform, methanol and acetic acid at a ratio of 3:1:0.5) to give 10.2 g of N,N-bis(2-hydroxy-3-octadecyloxypropyl)-L-arginine hydrochloride (yield 12.3%).

TLC (mixture of butanol, acetic acid and water at a ratio of 4:1:2): Rf=0.72 ESI mass spectrum: 827.7 (MH+) IR (NaCl, cm$^{-1}$): 3175, 2955, 2917, 2851, 1692, 1628, 1468, 1377, 1215, 1121

Example 5

Nε-(2-hydroxy-3-dodecyloxypropyl)-L-lysine hydrochloride

L-lysine hydrochloride (18.3 g, 0.1 mols) and 2.0 g (0.2 mols) of sodium hydroxide were dissolved in 100 ml of water in a three-necked round flask, and 100 ml of i-propanol were added thereto. Then, 24.2 g (0.1 mols) of dodecylglycidyl ether were added dropwise thereto over a period of 30 minutes while being heat-refluxed and stirred. Further, the mixture was stirred under reflux for 3 hours. It was identified through TLC and gas chromatography that dodecylglycidyl ether disappeared. Thereafter, the resulting mixture was neutralized with 10.1 g (0.1 mols) of 36% hydrochloric acid. The reaction solution was concentrated under reduced pressure, and the residue was purified through silica-gel column chromatography (Kieselgel 60, eluent= mixture of chloroform, methanol and acetic acid at a ratio of 3:1:0.5) to give 10.1 g of Nε-(2-hydroxy-3-dodecyloxypropyl)-L-lysine hydrochloride (yield 23.7%).

TLC (mixture of butanol, acetic acid and water at a ratio of 4:1:2): Rf=0.42 ESI mass spectrum: 389.4 (MH+) IR (NaCl, cm$^{-1}$): 2955, 2923, 2853, 1620, 1586, 1468, 1120

Example 6

L-lysine hydrochloride (18.3 g, 0.1 mols) and 2.0 g (0.2 mols) of sodium hydroxide were dissolved in 100 ml of water in a three-necked round flask, and 100 ml of i-propanol were added thereto. Then, 48.4 g (0.2 mols) of dodecylglycidyl ether were added dropwise thereto over a period of 30 minutes while being heat-refluxed ana stirred. Further, the mixture was stirred under reflux for 3 hours. It was identified through TLC and gas chromatography that dodecylglycidyl ether disappeared. Thereafter, the resulting mixture was neutralized with 10.1 g (0.1 mols) of 36% hydrochloric acid. The reaction solution was concentrated under reduced pressure, and the residue was purified through silica-gel column chromatography (Kieselgel 60, eluent= mixture of chloroform, methanol and acetic acid at a ratio of 3:1:0.5) to give 30.7 g of hydrochloride of an adduct of dodecylglycidyl ether and L-lysine at a ratio of 2:1 (yield 46.1%).

ESI mass spectrum: 631.6 (MH+) IR (NaCl, cm$^{-1}$): 2955, 2923, 2853, 1619, 1574, 1468, 1410, 1122

Example 7

Nε-(2-hydroxy-3-octadecyloxypropyl)-L-lysine hydrochloride

L-lysine hydrochloride (18.3 g, 0.1 mols) and 2.0 g (0.2 mols) of sodium hydroxide were dissolved in 100 ml of water in a three-necked round flask, and 100 ml of i-propanol were added thereto. Then, 32.6 g (0.1 mols) of octadecylglycidyl ether were added dropwise thereto over a period of 30 minutes while being heat-refluxed and stirred. Further, the mixture was stirred under reflux for 3 hours. It was identified through TLC and gas chromatography that octadecylglycidyl ether disappeared. Thereafter, the resulting mixture was neutralized with 10.1 g (0.1 mols) of 36% hydrochloric acid. The reaction solution was concentrated under reduced pressure, and the residue was purified through silica-gel column chromatography (Kieselgel 60, eluent= mixture of chloroform, methanol and acetic acid at a ratio of 3:1:0.5) to give 12.0 g of Nε-(2-hydroxy-3-octadecyloxypropyl)-L-lysine hydrochloride (yield 23.6%).

TLC (mixture of butanol, acetic acid and water at a ratio of 4:1:2): Rf=0.42 ESI mass spectrum: 473.5 (MH+) IR (NaCl, cm$^{-1}$): 2955, 2923, 2853, 1620, 1586, 1468, 1120

Example 8

L-lysine hydrochloride (18.3 g, 0.1 mols) and 2.0 g (0.2 mols) of sodium hydroxide were dissolved in 100 ml of water in a three-necked round flask, and 100 ml of i-propanol were added thereto. Then, 65.2 g (0.2 mols) of octadecylglycidyl ether were added dropwise thereto over a period of 30 minutes while being heat-refluxed and stirred. Further, the mixture was stirred under reflux for 3 hours. It was identified through TLC and gas chromatography that octadecylglycidyl ether disappeared. Thereafter, the resulting mixture was neutralized with 10.1 g (0.1 mols) of 36% hydrochloric acid. The reaction solution was concentrated under reduced pressure, and the residue was purified through silica-gel column chromatography (Kieselgel 60, eluent= mixture of chloroform, methanol and acetic acid at a ratio of 3:1:0.5) to give 40.3 g of hydrochloride of an adduct of octadecylglycidyl ether and L-lysine at a ratio of 2:1 (yield 48.3%).

ESI mass spectrum: 799.7 (MH+) IR (NaCl, cm$^{-1}$): 2955, 2923, 2853, 1619, 1574, 1468, 1410, 1122

Example 9

L-arginine was reacted with dodecylglycidyl ether in the same manner as in Example 1. After it was identified through TLC and gas chromatography that dodecylglycidyl ether disappeared, the reaction solution was neutralized with 36% hydrochloric acid. The reaction solution was concentrated under reduced pressure to give 47.3 g of a reaction mixture.

Example 10

L-lysine was reacted with dodecylglycidyl ether in the same manner as in Example 5. After it was identified through TLC and gas chromatography that dodecylglycidyl ether disappeared, the reaction solution was neutralized with 36% hydrochloric acid. The reaction solution was concentrated under reduced pressure to give 52.1 g of a reaction mixture.

Example 11

L-arginine (17.4 g, 0.1 mols) was dissolved in 100 ml of water in a three-necked round flask, and 100 ml of i-propanol were added thereto. Then, 25.6 g (0.1 mols) of Heroxine 8 (made by ACI Japan Ltd.) were added dropwise thereto over a period of 30 minutes while being heat-refluxed and stirred. Further, the mixture was stirred under reflux for 3 hours. After it was identified through TLC and gas chromatography that glycidyl ether disappeared, 12.9 g (0.1 mols) of DL-pyrrolidonecarboxylic acid were added thereto. Then, i-propyl alcohol was distilled off under reduced pressure, and the reaction solution was poured into cold acetone to give 50.9 g of a mixture of N-(2-hydroxy-3-dodecyloxy)propyl-L-arginine.DL-pyrrolidonecarboxylic acid salt and N-(2-hydroxy-3-tetradecyloxy) propyl-L-arginine.DL-pyrrolidonecarboxylic acid salt. The ESI mass spectrum of the resulting mixture was measured, and peaks of 417.5 (MH+) and 445.5 (MH+) were identified.

Example 12

With respect to the surfactants obtained in Examples 1 and 5 and trimethylstearylammonium chloride and N-cocoyl-L-arginine ethyl ester.DL-pyrrolidonecarboxylic acid salt as comparative examples, the primary irritations of the skin and the eye mucous membrane were measured by the following test methods. The results are shown in Table 1.

(1) Test for Primary Skin Irritation

Each of four New Zealand white male rabbits was seal-coated with a patch test plaster permeated with 0.3 ml of a 1% surfactant aqueous solution, and was allowed to stand for 24 hours. Then, the plaster was removed from the rabbit. After 24 hours, the irritation was evaluated according to the following Draise's evaluation standard.

| Draise's evaluation score | Irritation level |
| --- | --- |
| 4 or more | heavy |
| from 2 to less than 4 | light |
| less than 2 | slight |

(2) Test for Primary Eye Mucous Membrane Irritation

The lower eyelids of both eyes of each of four New Zealand white male rabbits were formed into a bag shape, and 0.1 ml of a 1% surfactant aqueous solution were dropped therein. Thereafter, the upper and lower eyelids were gently joined. The irritation was evaluated according to the following Draise's evaluation standard 24 hours after addition of the drops.

| Draise's evaluation score | Irritation level |
| --- | --- |
| 50 or more | heavy |
| from 20 to less than 50 | medium |
| from 10 to less than 20 | light |
| less than 10 | slight |

TABLE 1

| | | Irritation | |
| --- | --- | --- | --- |
| | | Skin | Mucous membrane |
| Examples | Compound in Example 1 | slight | slight |
| | Compound in Example 5 | slight | slight |
| Comparative Examples | trimethylstearylammonium chloride | heavy | medium |
| | Nα-cocoyl-L-arginine ethyl ester salt | slight | slight |

From Table 1, it becomes apparent that the surfactant of the present invention gives a low level of irritation.

Example 13

The surfactants were measured for the bubbling power and the bubble stability by the following test methods.

Tests for bubbling power and bubble stability:

Each of the surfactants was adjusted with purified water such that the concentration of the activator reached 0.25% by weight. Fifty grams of the aqueous solution were charged into a 350-milliliter home mixer, and stirred for 5 seconds. The volume (ml) of the bubbles immediately after the stirring and the volume (ml) of the bubbles after 5 minutes of the stirring were measured. The volume of bubbles immediately after the stirring was defined as a bubbling power, and the bubble retention calculated from the following equation was defined as a bubble stability.

Bubble retention (%)=(volume of bubbles after 5 minutes of stirring/volume of bubbles immediately after stirring)× 100

TABLE 2

| | | Bubbling power (ml) | Bubble stability (%) |
| --- | --- | --- | --- |
| Examples | Compound in Example 1 | 150 | 80.0 |
| | Compound in Example 5 | 130 | 69.2 |
| Comparative Examples | N-(2-hydroxy-3-dodecyloxypropyl)methyltaurine sodium salt | 80 | 37.5 |
| | N-(2-hydroxy-3-dodecyloxypropyl) sarcosine sodium salt | 120 | 58.3 |
| | Coconut oil fatty acid amide propyl betaine solution | 140 | 64.3 |
| | N-coconut oil fatty acid-L-glutamic acid triethanolamine | 130 | 61.5 |

From Table 2, it becomes apparent that the surfactant of the present invention exhibits the bubbling power which is the same as, or higher than, that of the usual surfactant which exhibits a low level of irritation.

Example 14

The solubility of each surfactant in water was tested by the following method.

Each of the surfactants was diluted with water to a concentration of 1, 3, 5, 10 or 20% by weight, and the solution was rendered uniform while being stirred at 50° C. The resulting solution was allowed to stand overnight at 25° C., and the solubility was then visually measured. The results are shown in Table 3.

TABLE 3

| | | 1% | 3% | 5% | 10% | 20% |
| --- | --- | --- | --- | --- | --- | --- |
| Invention | Compound in Example 1 | clear | clear | clear | clear | clear |
| Comparative Example | N-(2-hydroxy-hexadecyl)-L-arginine hydrochloride | slightly turbid | turbid | milk-white | milk-white | milk-white |

From Table 3, it becomes apparent that the compound of the present invention exhibits a higher solubility in water. Accordingly, a toiletry or detergent composition having a higher solution stability can be formed therefrom because separation or precipitation of the surfactant component can be prevented effectively.

Example 15

A 0.5% surfactant aqueous solution (150 g) was prepared. A hairpiece made of 20 g of the healthy hair of a Japanese woman was washed with a 1% lauryl ether sodium sulfate aqueous solution, and then dipped in the above-mentioned aqueous solution for 1 minute. The resulting hairpiece was gently rinsed with running hot water, and then dried using a dryer. With respect to softness, combing property, moist feeling and sticky feeling of the hair after drying, the organoleptic evaluation was conducted by 8 expert panelists. In the evaluation, average values were calculated on the basis of the following standard. When the average value was 4.5 or more, the property was evaluated as very good (⊚). When the average value was between 3.5 and 4.4, the property was evaluated as good (○). When the average value was between 2.5 and 3.4, the property was evaluated as common (Δ). When the average value was 2.4 or less, the property was evaluated as bad.

<Evaluation standard>

Softness of the hair:
5: very soft and smooth
4: soft
3: common
2: slightly hard
1: hard Combing property of the hair:
5: Combing is conducted well and quite smoothly.
4: Combing is conducted well.
3: Combing property is common.
2: Combing property is slightly bad.
1: Combing property is bad, and combing is sometimes interrupted.

Moist feeling:
5: quite moist
4: moist
3: common
2: slightly dry and hard
1: quite dry and hard Sticky feeling:
5: not sticky
4: little sticky
3: common
2: slightly sticky
1: sticky

TABLE 4

|  | Example Compound in Example 1 | Comparative Example (N-(2-hydroxyhexa-decyl)-L-arginine hydrochloride | Untreated |
|---|---|---|---|
| Softness | ⊚ | ○ | bad |
| Combing property | ○ | Δ | bad |
| Moist feeling | ⊚ | ○ | bad |
| Sticky feeling | ○ | ○ | bad |

Example 16

A detergent composition shown in Table 5 was prepared. Each of eight expert panelists washed the hair with a commercially available shampoo, and then used the detergent composition. With respect to a softness, a combing property, a moist feeling and a sticky feeling of the hair after drying, the organoleptic evaluation was conducted by them. In the evaluation, average values were calculated on the basis of the following standard. When the average value was 4.5 or more, the property was evaluated as very good (⊚). When the average value was between 3.5 and 4.4, the property was evaluated as good (○). When the average value was between 2.5 and 3.4, the property was evaluated as common (Δ). When the average value was 2.4 or less, the property was evaluated as bad (X).

<Evaluation standard>

Softness of the hair:
5: very soft and smooth
4: soft
3: common
2: slightly hard
1: hard Combing property of the hair:
5: Combing is conducted well and quite smoothly.
4: Combing is conducted well.
3: Combing property is common.
2: Combing property is slightly bad.
1: Combing property is bad, and combing is sometimes interrupted.

Moist feeling:
5: quite moist
4: moist
3: common
2: slightly dry and hard
1: quite dry and hard Sticky feeling:
5: not sticky
4: little sticky
3: common
2: slightly sticky
1: sticky

TABLE 5

|  | Examples | | | | | | | Comparative Examples | | | | | | |
|---|---|---|---|---|---|---|---|---|---|---|---|---|---|---|
| Surfactant in Production Example 1 | 1.0 | | | | | | | | | | | | | |
| Surfactant in Production Example 2 | | 1.0 | | | | | | | | | | | | |
| Surfactant in Production Example 3 | | | 1.0 | | | | | | | | | | | |
| Surfactant in Production Example 5 | | | | 1.0 | | | | | | | | | | |
| Surfactant in Production Example 8 | | | | | 1.0 | | | | | | | | | |
| Surfactant in Production Example 10 | | | | | | 1.0 | | | | | | | | |
| Surfactant in Production Example 11 | | | | | | | 1.0 | | | | | | | |
| N-(2-hydroxy-3-dodecyloxypropyl)serine | | | | | | | | 1.0 | | | | | | |
| N-(2-hydroxy-3-dodecyloxypropyl)methyltaurine | | | | | | | | | 1.0 | | | | | |
| N-(2-hydroxy-3-dodecyloxypropyl)sarcosine | | | | | | | | | | 1.0 | | | | |
| Trimethylstearylammonium chloride | | | | | | | | | | | 1.0 | | | |
| Dimethyldistearylammonium chloride | | | | | | | | | | | | 1.0 | | |
| Nα-cocoyl-L-arginine ethyl ester | | | | | | | | | | | | | 1.0 | |

TABLE 5-continued

|  | Examples | | | | | | | Comparative Examples | | | | | |
| --- | --- | --- | --- | --- | --- | --- | --- | --- | --- | --- | --- | --- | --- |
| Cetanol | 3.0 | 3.0 | 3.0 | 3.0 | 3.0 | 3.0 | 3.0 | 3.0 | 3.0 | 3.0 | 3.0 | 3.0 | 3.0 |
| Propylene glycol | 1.0 | 1.0 | 1.0 | 1.0 | 1.0 | 1.0 | 1.0 | 1.0 | 1.0 | 1.0 | 1.0 | 1.0 | 1.0 |
| Purified water | * | * | * | * | * | * | * | * | * | * | * | * | * |
| ORGANOPEPTIC EALUATION | | | | | | | | | | | | | |
| Softness | ⊚ | ⊚ | ⊚ | ⊚ | ○ | ⊚ | ⊚ | x | x | x | ⊚ | ○ | Δ |
| Combing property | ○ | ⊚ | ○ | ○ | ○ | ○ | ○ | x | x | x | ○ | ○ | Δ |
| Moist feeling | ⊚ | ⊚ | ⊚ | ○ | ○ | ⊚ | ○ | x | x | x | Δ | ○ | ⊚ |
| Sticky feeling | ○ | Δ | ○ | ○ | Δ | ○ | ○ | x | x | x | ○ | Δ | x |

*balance

From Tables 4 and 5, it becomes apparent that the surfactant and the detergent composition of the present invention exhibit excellent conditioning effects.

Example 17

Shampoo

A composition shown in each of Tables 6 and 7 was heat-dissolved at from 70 to 80° C., and then cooled to room temperature to obtain a shampoo. This shampoo exhibited an excellent rinsing property, and feeling after cleaning was satisfactory.

TABLE 6

| Composition | Amount |
| --- | --- |
| Compound in Example 1 | 5.0 |
| N-cocoyl-L-glutamic acid TEA | 2 |
| Polyoxyethylene (3) lauryl ether sodium sulfate | 10 |
| Lauric acid monoethanolamide | 1 |
| Propylene glycol | 5 |
| Cationic polymer ("MERQUAT 100" made by MERCK & Co., Inc.) | 0.3 |
| Antiseptic | 0.1 |
| Perfume | 0.1 |
| EDTA sodium salt | 0.1 |
| Purified water | balance |

TABLE 7

| Composition | Amount |
| --- | --- |
| Compound in Example 5 | 1.0 |
| Lauric acid amide propylbetaine | 15 |
| Coconut oil fatty acid diethanolamide | 5 |
| DL-pyrrolidonecarboxylic acid sodium salt | 5 |
| Ampholytic polymer ("PLAS SIZE L-401" made by GOO Chemical Co., Ltd.) | 0.8 |
| Citric acid | |
| Antiseptic | 0.5 |
| Perfume | 0.1 |
| Purified water | 0.1 balance |

Example 18

Rinse

A composition shown in each of Tables 8 to 10 was heat-dissolved at from 70 to 80° C., and then cooled to room temperature to obtain a rinse. This rinse exhibited an excellent rinsing property, and feeling after drying was satisfactory.

TABLE 8

| Composition | Amount |
| --- | --- |
| Compound in Example 11 | 5 |
| Polyoxyethylene (3) sulfosuccinic acid sodium salt | 5 |
| Cocoylisethionic acid sodium salt | 2 |
| Pyroglutamic acid glyceryl oleate | 1 |
| N-lauroyl-β-alanine TEA | 1 |
| Polyethylene glycol monostearate | 0.5 |
| Emorient oil ("Eldew CL-301" made by Ajinomoto Co., Inc.) | 3 |
| Wetting agent ("Prodew 100" made by Ajinomoto Co., Inc.) | 5 |
| Antiseptic | 0.1 |
| Perfume | 0.1 |
| Purified water | balance |

TABLE 9

| Compound | Amount |
| --- | --- |
| Compound in Example 3 | 1 |
| Isostearic acid diethanolamide | 2 |
| Cetanol | 2 |
| Liquid paraffin | 1 |
| Polyoxyethylene (5) oleyl ether | 0.3 |
| 1,3-butylene glycol | 5 |
| Trimethylstearylammonium chloride | 0.1 |
| Hydroxyethyl cellulose | 0.5 |
| Antiseptic | 0.1 |
| Perfume | 0.1 |
| Purified water | balance |

TABLE 10

| Composition | Amount |
| --- | --- |
| Compound in Example 5 | 6 |
| Cetanol | 6 |
| Glycerol | 3 |
| Partially deacetylated chitin | 0.5 |
| Polyoxyethylene (20) sorbitan monostearate | 0.2 |
| Antiseptic | 0.1 |
| N-laurolyllysine | trace |
| Purified water | balance |

Example 19

Hair Conditioner

A composition shown in each of Tables 11 and 12 was heat-dissolved at from 70 to 80° C., and then cooled to room temperature to obtain a hair conditioner.

TABLE 11

| Composition | Amount |
| --- | --- |
| Compound in Example 2 | 1 |
| Cetanol | 5 |
| Coconut oil fatty acid diethanolamide | 4 |
| Dimethylpolysiloxane (1,000 cs) | 1 |
| Polyethylene glycol (400) | 0.2 |
| vaseline | 0.5 |
| Self-emulsifiable glycerol monostearate | 0.2 |
| Glycerol | 1 |
| Hydroxyethyl cellulose | 0.8 |
| Antiseptic | 0.2 |
| Purified water | balance |

TABLE 12

| Composition | Amount |
| --- | --- |
| Compound in Example 6 | 5 |
| Behenyl alcohol | 7 |
| Isopropyl myristate | 1 |
| Dipropylene glycol | 3 |
| Polyoxyethylene (4) stearyl ether | 5 |
| Polyethylene glycol dioleate | 0.5 |
| Polyethylene glycol | 0.5 |
| Sodium lactate | 0.1 |
| Antiseptic | 0.1 |
| Purified water | balance |

Example 20

Hair Lotion

A composition shown in Table 13 was heat-dissolved at from 40 to 50° C., and then cooled to room temperature to obtain a hair lotion.

TABLE 13

| Compound | Amount |
| --- | --- |
| Compound in Example 5 | 0.05 |
| Oleyl alcohol | 0.2 |
| Liquid paraffin | 0.5 |
| Ethanol | 5 |
| Sorbitol | 4 |
| Polyoxyethylene (20) lauryl ether | 2.5 |
| sorbitan monolaurate | 0.5 |
| Pigment | 0.1 |
| Perfume | 0.1 |
| Antiseptic | 0.1 |
| Purified water | balance |

Example 21

A commercially available cotton towel and an acryl jersey were washed twice with a commercially available clothing detergent using an electric washing machine (a double-tank type). Thereafter, the towel and jersey rinsed with city water of ordinary temperature. Each of the surfactants were adjusted with city water at a temperature of 25° C. such that the concentration of the surfactant reached 50 ppm and a homogeneous solution was obtained. The cotton towel and acryl jersey, which have equal weights, soaked in the surfactant solution having a weight 30 times greater than the combined weight of the cotton towel and acryl jersey. After 3 minutes, the towel and jersey were dehydrated using the electric washing machine. Thereafter, they were dried at a temperature of 25° C. and a relative humidity of 40% for 24 hours, and thereafter evaluated.

(1) Test for Fabric Softness

With respect to softness, the organoleptic evaluation was conducted by eight panelists. In the evaluation, average values were calculated on the basis of the following standard.

<Evaluation standard>

4: equal to distearyl dimethyl ammonium chloride

3: softer than trimethyl stearyl ammonium chloride

2: equal to trimethyl stearyl ammonium chloride

1: equal to untreated (2) Test for Hygroscopic Property

According to JIS (Japan Industrial Standard) L 1096, a cotton towel treated with each of the surfactants was cut into a rectangular fragment (20 mm×150 mm), and the end part of the fragment (5 mm) were soaked in the water colored by blue dye. After five minutes, the height of ascended water was measured.

TABLE 14

| | Surfactant | Softness | Hygroscopic (mm) |
| --- | --- | --- | --- |
| Comparative Example | Distearyl dimethyl ammonium chloride | 4 | 25 |
| Example | Trimethyl stearyl ammonium chloride | 2 | 37 |
| | Surfactant in Example 11 | 4 | 77 |
| | Surfactant in Example 7 | 4 | 80 |
| | Surfactant in Example 8 | 4 | 77 |
| | Surfactant in Example 10 | 3 | 77 |

Example 22

Fabric Softener

A composition shown in each of Tables 15 and 16 was heat-dissolved at from 70 to 80° C., and then cooled to room temperature to obtain a fabric softener. This fabric softener exhibited an excellent softening property, and the hygroscopic property of fabric treated with it was satisfactory.

TABLE 15

| Composition | Amount |
| --- | --- |
| Compound in Example 11 | 15.0 |
| Glyceryl monostearate | 7.5 |
| Stearic acid | 1.0 |
| Sodium chloride | 0.2 |
| Glycerol | 2.0 |
| Ethanol | 5.0 |
| Polyethylene glycol 400 | 2.5 |
| | 0.1 |
| Pigment | 0.1 |
| Perfume | 0.1 |
| Antiseptic | balance |
| Purified water | |

TABLE 16

| Composition | Amount |
| --- | --- |
| Compound in Example 8 | 7.5 |
| Sorbitan monostearate | 7.5 |
| Stearic acid | 0.5 |
| Sodium chloride | 0.2 |
| Ethylene glycol | 5.0 |
| Polyethylene glycol 400 | 1.0 |
| Pigment | 0.1 |

TABLE 16-continued

| Composition | Amount |
| --- | --- |
| Perfume | 0.1 |
| Antiseptic | 0.1 |
| Purified water | balance |

Obviously, numerous modifications and variations of the present invention are possible in light of the above teachings. It is therefore to be understood that within the scope of the appended claims, the invention may be practiced otherwise than as specifically described herein.

This application is based on Japanese Patent Application No. 20126/1996 filed with the Japanese Patent Office on Feb. 6, 1996, the entire contents of which are herein incorporated by reference.

What is claimed as new and desired to be secured by Letters Patent of the United States is:

1. A surfactant comprising a basic amino-acid derivative or a salt thereof, wherein the surfactant is obtained by heat-reacting a basic amino acid or a salt thereof with a glycidyl ether in an alcohol or in a mixed solvent of an alcohol and water,
   wherein said basic amino acid is selected from the group consisting of arginine, lysine, ornithine, histidine, hydroxylysine and mixtures thereof, and wherein said glycidyl ether has a linear or branched alkyl or alkenyl group having from 8–22 carbon atoms.

2. The surfactant of claim 1, wherein said glycidyl ether is selected from the group consisting of decylglycidyl ether, stearylglycidyl ether, dodecylglycidyl ether, tetradecylglycidyl ether and a mixture thereof.

3. The surfactant of claim 1, wherein said salt of the basic amino acid is an alkali metal salt.

4. The surfactant of claim 1, wherein said alcohol is a lower alcohol.

5. The surfactant of claim 1, wherein said alcohol is selected from the group consisting of methyl alcohol, ethyl alcohol, n-propyl alcohol, i-propyl alcohol and a mixture thereof.

6. The surfactant of claim 1, wherein a mixing ratio of said alcohol to water in said mixed solvent is between 100:0 and 10:90.

7. The surfactant of claim 1, wherein a mixing ratio of said alcohol to water in said mixed solvent is between 1:1 and 2:1.

8. The surfactant of claim 1, wherein said heat-reacting step is conducted at a temperature between 80° C. and 95° C.

9. The surfactant of claim 1, wherein said heat-reacting step is conducted under alkaline conditions.

10. The surfactant of claim 1, wherein said basic amino acid is arginine.

11. The surfactant of claim 1, wherein said basic amino acid is lysine.

12. The surfactant of claim 1, wherein said basic amino acid is ornithine.

13. The surfactant of claim 1, wherein said basic amino acid is histidine.

14. The surfactant of claim 1, wherein said basic amino acid is hydroxylysine.

15. The surfactant of claim 1, wherein said basic amino acid is said mixture thereof.

16. A fabric softener composition comprising said surfactant of claim 1 or a salt thereof.

* * * * *